United States Patent [19]

Harkness

[11] Patent Number: Plant 5,582

[45] Date of Patent: Dec. 3, 1985

[54] NEW ROSE PLANT

[76] Inventor: John L. Harkness, 1 Bank Alley, Southwold, Suffolk IP18 6JD, England

[21] Appl. No.: 592,406

[22] Filed: Mar. 22, 1984

[51] Int. Cl.[4] ..... A01H 5/00

[52] U.S. Cl. ..... Plt./22

[58] Field of Search ..... Plt./24, 22

*Primary Examiner*—Robert E. Bagwill
*Attorney, Agent, or Firm*—Vincent G. Gioia

[57] ABSTRACT

A new floribunda rose variety with flowers of apricot coloring.

1 Drawing Figure

1

The present invention relates to a new and distinct variety of rose plant of the floribunda rose class, which was originated by my crossing as seed parent the rose known as "Southampton" and as pollen parent the rose known as "Typhoon". The denomination of the new rose is "Harroony".

Among the novel characteristics possessed by this new variety which distinguish it from its parents and all other varieties of which I am aware are flowers of unusual apricot coloring borne in large sprays and of substantially unfading character. The flowers embody various tones of apricot and are attractively displayed against dense, dark green foliage having a holly-like appearance. The flower's unique coloring is highlighted by the good floribunda inflorescence form borne on a plant of unusually good disease resistance for a cultivar of this color range. Asexual reproduction by budding of the new variety as performed in Clackamas County, Ore., shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (R.H.S.C.C.). The terminology used in color description herein refers to plate numbers in the aforementioned color chart, e.g., "168D" is plate 168D of The Royal Horticultural Society Colour Chart.

Parentage: Seedling.
*Seed parent.*—"Southampton".
*Pollen parent.*—"Typhoon".
Class: Floribunda.

The following observations are made of specimens grown outdoors in Clackamas County, Ore., during the month of September.

FLOWER

Blooming habit: Continuous.

A. Bud:
- (1) *Size.*—Medium.
- (2) *Form.*—Ovoid.
- (3) *Color.*—When sepals first divide — near 168D quickly lightening to near 24D.

2

- (4) *Sepals.*—Slightly longer than bud, numerous glandular hairs on back and edges.
- (5) *Peduncle.*—Length — Short, 1½ to 2 inches. Aspect — Straight. Strength — Strong, erect. Color — Near 144B.

B. Bloom:
- (1) Size.—Average size when fully expanded — about 4 inches.
- (2) *Borne.*—Several together in large sprays.
- (3) *Form.*—Cup shaped — Ruffled.
- (4) *Petalage.*—Number of petals under normal conditions — about 30.
- (5) *Color.*—As sepals fall, the color of the undersurface of the first petals is near 168D. When the petals unfurl, the apricot coloring becomes more obvious and is deepest in color tone (near 168C) where petals remain bunched in ⅓ to ½ open blooms. As the flower opens further, the color of the outer petals appears generally paler. The coloring of the petals' undersurfaces approaches 23D. The coloring remains stable as the blooms age displaying a generally apricot tonality.

C. Petals:
- (1) *Texture.*—Thick.
- (2) *Appearance.*—Satiny inside and outside.
- (3) *Form.*—Rounded triangular.
- (4) *Arrangement.*—Regular.
- (5) *Petaloids in center.*—Medium.
- (6) *Persistence.*—Drop off cleanly.
- (7) *Fragrance.*—Slight, musk.
- (8) *Lasting quality.*—Long lasting on plant, short-lived as cut flower.

REPRODUCTIVE ORGANS

A. Stamens, filaments and anthers:
- (1) *Arrangement.*—Regularly arranged around styles, long, incurved.
- (2) *Color.*—Filaments near 23A.

B. Pollen:
- *Color.*—Near 24B.

C. Styles: Few, tightly bunched, short, color near 33A.

D. Stigmas:
- *Color.*—Near 12C.

E. Hips:
- *Shape.*—Large globular.
- *Size.*—Large.
- *Color.*—Near 14B.
- *Do seeds protrude?*—No.

PLANT

A. Form: Compact.

B. Growth: Vigorous, densely branched.
*Height attained.*—About 30 inches.

C. Foliage: Compound 5 to 7 leaflets.
(1) *Size.*—Large.
(2) *Quantity.*—Abundant.
(3) *Color.*—New foliage: Upper side — Near 53A. Under side — Near 53B. Old foliage: Upper side — Near 147A. Under side — Near 146D.
(4) *Shape.*—Oval, acuminate.
(5) *Texture.*—Upper side is leathery, glossy with prominent veins and under side is dull.
(6) *Edge.*—Serrate.
(7) *Serration.*—Simple.
(8) *Leaf stem.*—Color — Near 144C. Under side — Near 145B.
(9) *Stipules.*—Short, broad, slightly serrate.
(10) *Resistance to disease.*—Blackspot — Excellent. Mildew — Good. Rust — Excellent.

D. Wood:
(1) New wood.—Color — Near 153C. Bark — Smooth, shiny.
(2) *Old wood.*—Color — Near 144A. Bark — Smooth, shiny.

E. Thorns:
(1) *Thorns.*—Quantity (main stalk): ordinary. On laterals from stalk — Few. Form — Relatively large, straight. Length — Medium. Color — Near 163C. Position — Regular.
(2) *Prickles.*—Few to none.

F. Winter hardiness: Needs ordinary winter protection.

I claim:

1. A new and distinct variety of rose plant of the floribunda class, substantially as shown and described, characterized particularly by flowers of unique apricot coloring having unusually good disease resistance for plants with flowers of this color range and attractive dark green, holly-like foliage.

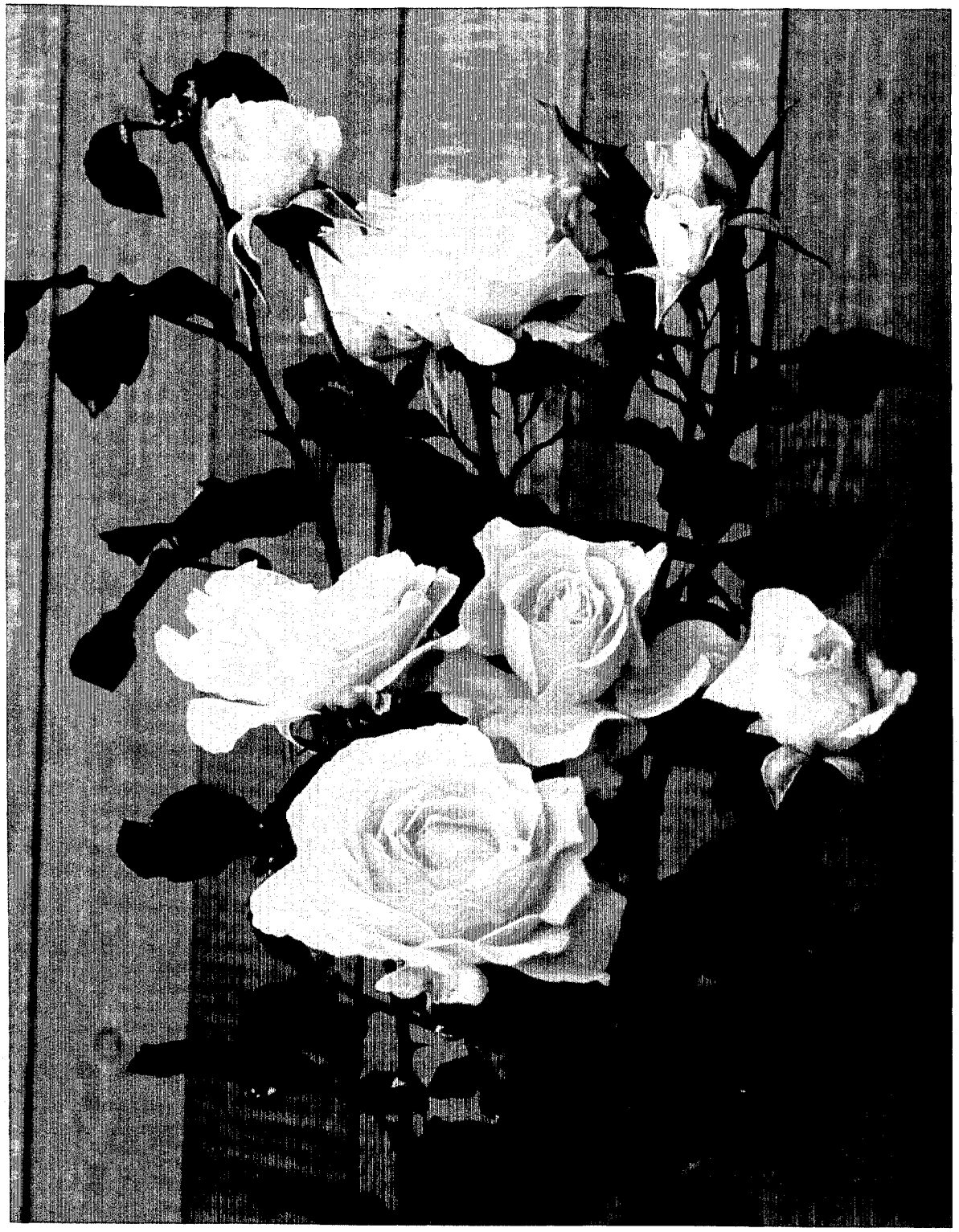

* * * * *